(12) United States Patent
Blake et al.

(10) Patent No.: US 6,275,560 B1
(45) Date of Patent: Aug. 14, 2001

(54) CARDIAC GATED COMPUTED TOMOGRAPHY SYSTEM

(75) Inventors: James A. Blake, Franklin; Robert F. Senzig, Germantown, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/218,352

(22) Filed: Dec. 22, 1998

(51) Int. Cl.$^7$ .................................................... A61B 6/00
(52) U.S. Cl. .................................................. 378/8; 378/95
(58) Field of Search ........................................ 378/4, 8, 95

(56) References Cited

U.S. PATENT DOCUMENTS

| | | | |
|---|---|---|---|
| 4,182,311 | * | 1/1980 | Seppi et al. ............................ 378/9 X |
| 4,206,363 | * | 6/1980 | Hounsfield et al. ...................... 378/8 |
| 4,504,895 | | 3/1985 | Steigerwald . |
| 4,530,109 | * | 7/1985 | Klausz ................................... 378/8 |
| 4,547,892 | * | 10/1985 | Richey et al. ............................ 378/8 |
| 4,689,670 | * | 8/1987 | Okazaki ................................ 378/8 X |
| 5,291,402 | | 3/1994 | Pfoh . |
| 5,751,782 | | 5/1998 | Yoshitome . |
| 5,828,718 | | 10/1998 | Ruth et al. . |
| 5,832,051 | | 11/1998 | Lutz . |

FOREIGN PATENT DOCUMENTS

| | | |
|---|---|---|
| 196 27 166 A1 | 1/1997 | (DE) . |
| 0 370 341 | 5/1990 | (EP) . |
| 0 471 455 | 2/1992 | (EP) . |
| 2036520 | 6/1980 | (GB) . |

OTHER PUBLICATIONS

A. Fiorino, "Electron–beam computed tomography, coronary artery calcium, and evaluation of patients with coronary artery disease," Annals of Internal Medicine 128:839–847, May 15, 1998.

G. Cowley, "Are you headed for a heart attack despite your low cholesterol? A $400 test makes it easier to find out," Newsweek, Apr. 6, 1998.

Y. Arad, et al., "The predictive value of electron beam CT of the coronary arteries: 19 month follow–up of 1173 asymptomatic subjects," Circulation 93(11) 1951–3, Jun. 1, 1996.

C. Woodhouse, et al., "Coronary Arteries: Respective Cardiac Gating Technique to Redcuce Cardiac Motion Artifact at Spiral CT," Radiology 204(2) 566–569 (1997).

D. Parker, "Optimal short scan convolution reconstruction for fan–beam CT," Med. Phys. (9) 254–257 (1982).

* cited by examiner

Primary Examiner—David P. Porta
(74) Attorney, Agent, or Firm—Armstrong Teasdale LLP; Christian G. Cabou

(57) ABSTRACT

The present invention, in one form, is an imaging system which synchronizes the emission of x-rays and the collection of data to a heart cycle to provide improved image quality. In one embodiment, the imaging system utilizes a synchronization unit to determine a selected heart period and to control generation of x-ray beams during the selected period. As the x-ray beams are emitted toward a detector, data is collected for a view angle. As the heart continues to cycle, data for a series of view angles is collected so that an image of the heart during the selected period is generated.

14 Claims, 2 Drawing Sheets

CARDIAC GATED COMPUTED TOMOGRAPHY SYSTEM

BACKGROUND OF THE INVENTION

This invention relates generally to computed tomography (CT) imaging and more particularly, to a cardiac gated CT system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

With known CT system, projection data is collected from a helical or axial scan to generate sequential frames of images of an area, or organ, within a patient. A frame corresponds to a two dimensional slice taken through the imaged object, e.g., the patient. Typically, an operator attempts to minimize the amount of time required to generate each frame to minimize motion related image degradation.

At least one known CT system, images of a patient's heart are generated and reviewed to identify certain types of conditions. However, as a result of the movement of the heart and the blood, the heart images are blurred. The blurring causes difficulty in identifying conditions within the heart.

To improve the quality of the images, it is desirable to provide an imaging system which gathers data during a selected period of a heart cycle. It would also be desirable to provide such a system which controls the emission of x-rays to reduce the x-ray dosage to the patient.

BRIEF SUMMARY OF THE INVENTION

These and other objects may be attained by an imaging system which, in one embodiment, synchronizes the emission of x-rays and the collection of data to a selected portion of a heart cycle to provide improved image quality. In an exemplary embodiment, the imaging system utilizes an synchronization unit to determine the selected period of the heart and to generate a short burst of x-ray beams during the selected period. As the x-ray beams are emitted toward a detector array, data is collected for a view angle. As the heart continues to cycle, data is collected for a series of view angles so that a complete image of the heart during the selected period is generated.

The above described imaging system gathers data during a selected period of the heart cycle so that image quality is improved. In addition, the imaging system controls the emission of x-ray beams so that x-ray dosage to the patient is reduced.

DETAILED DESCRIPTION OF THE INVENTION

Figure 1:
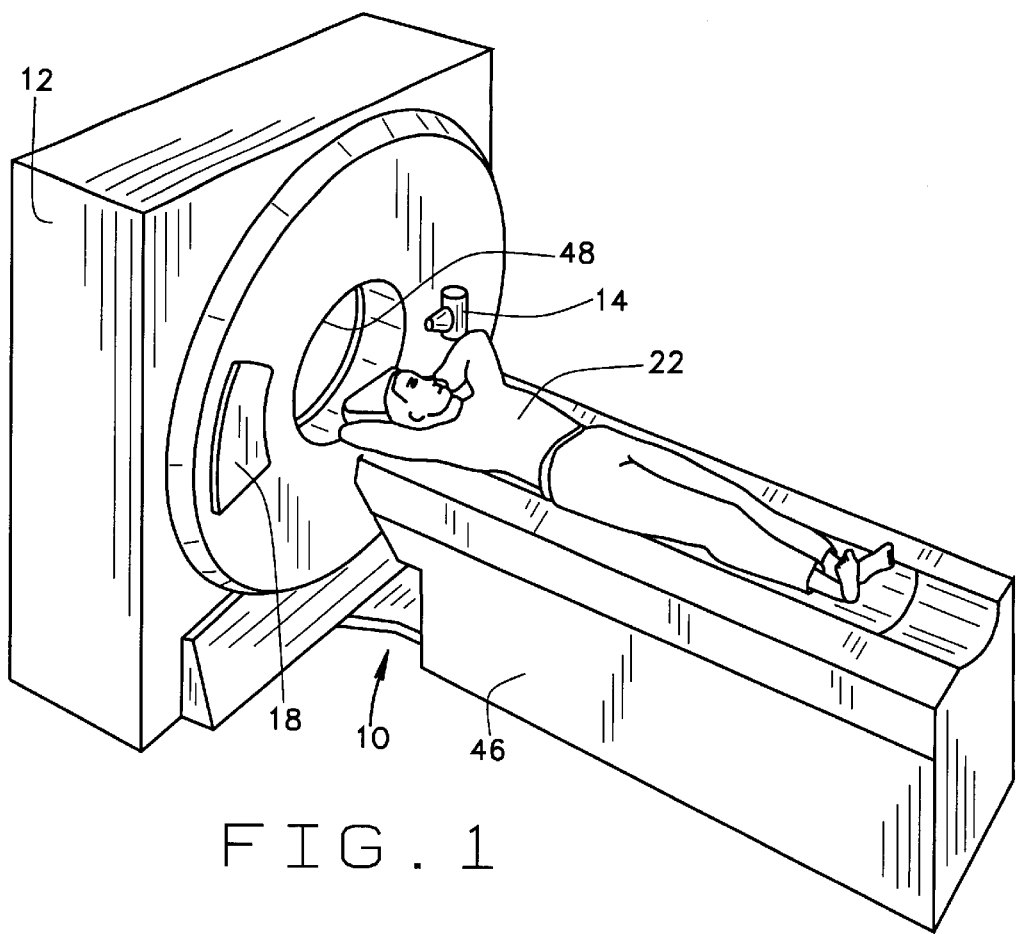
FIG. 1 is a pictorial view of a CT imaging system.
Figure 2:
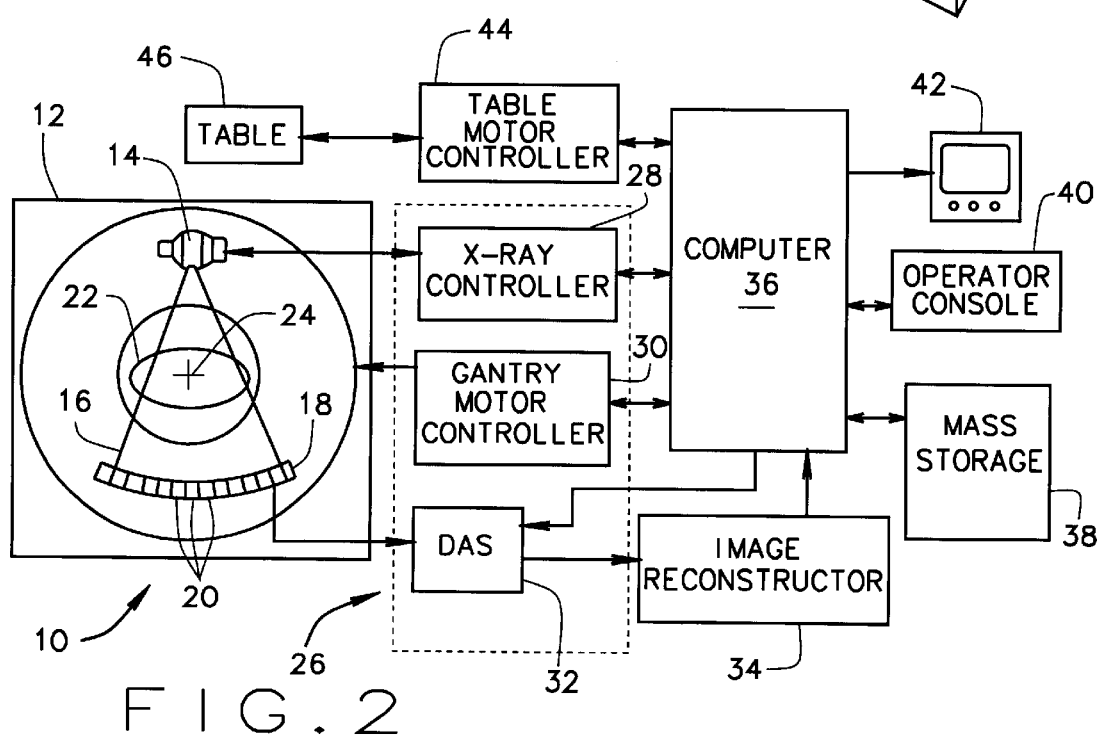
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment of the present invention, a synchronization unit, or circuit 100 is utilized to synchronize short bursts of x-ray beams to occur during a selected position, or period, of a heart cycle of a patient. Data collected from a series of these short bursts of x-rays are then utilized to generate an image of the object. The image provides a complete image of the object during the selected period of the heart cycle. As a result, for example by collecting the data during a resting period of the heart, image quality is improved.

Figure 3:
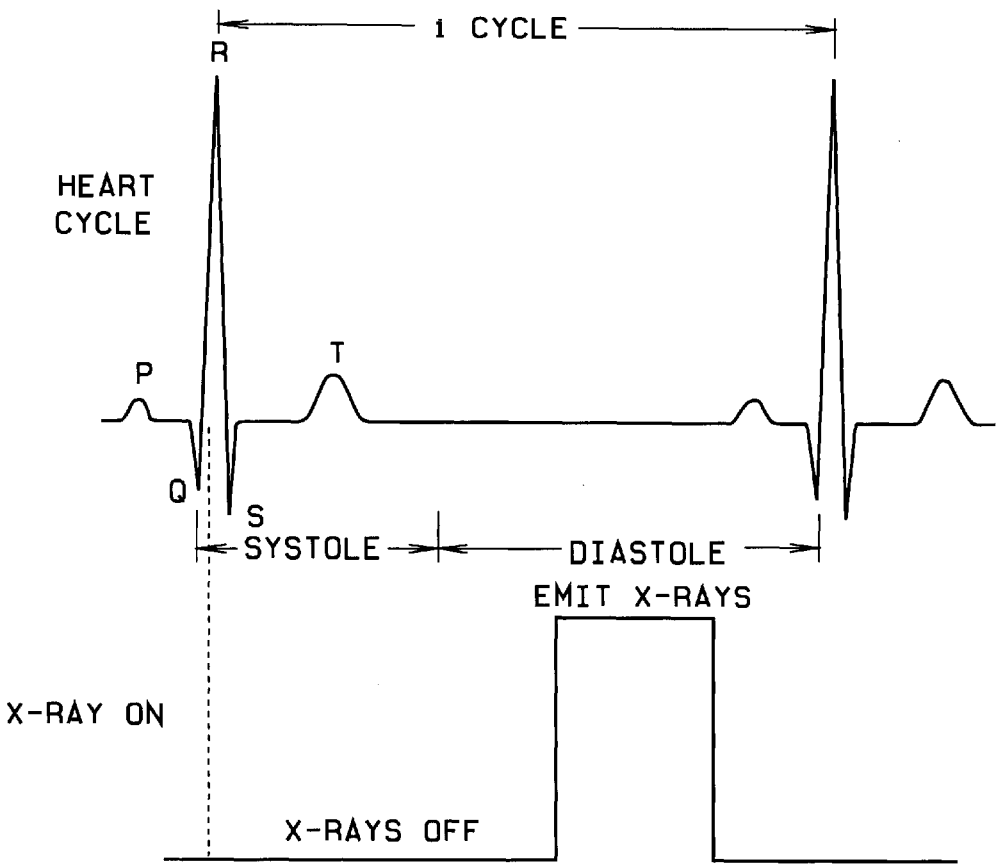
FIG. 3 is an EKG signal waveform.

More specifically, circuit 100 measures, or detects, the electrical activity of a heart of patient 22 to determine the cycle of a patient's heart. In one embodiment, an output signal of at least one electrode attached to patient 22 is coupled to an electronic amplifier (not shown) which generates a heart cycle signal. The heart cycle signal, may for example, be generated by an EKG system or exercise monitor, as known in the art. For example, and as shown in FIG. 3, an EKG system generates a heart cycle signal waveform using at least one of the electrode output signals. The heart cycle signal waveform, illustrates one cardiac cycle including a systole condition, or period, and a diastole condition, or period of the heart. The portion of the signal which is labeled Q, R and S is referred to as the QRS complex, in which the R-feature, or R-wave, is the most prominent, highest amplitude, feature of the entire signal. The cardiac cycle is typically defined as beginning with a R-wave and continuing until the occurrence of the next R-wave.

Heart functions are characterized by two distinct periods called systole and diastole. In systole, the heart muscle is contracting the volume of the left ventricle to pump the contents out through the aortic valve. During the diastole, or diastolic period, the left ventricle is filling through the mitral valve. At the end of the systole, the left ventricle has its smallest volume since it has been contracted to pump blood out. The end of the diastole is the point at which the left ventricle has its largest volume since it is filled with blood ready to be pumped out. During the diastolic period the heart is relatively motion-free allowing images generated from data collected during this period to be clearer as a result of the limited movement.

Utilizing the heart cycle signal, an x-ray-on, or gating, signal is generated by circuit 100 to determine the timing and duration of data collection. In one embodiment, circuit 100 transitions the state of the x-ray-on signal after delaying a selected period of time from the heart cycle representing the selected portion of the heart. As a result of transitioning the x-ray-on signal, x-ray beam 16 are emitted during the selected period of the heart cycle. More specifically, the x-ray-on gating output signal of circuit 100 is coupled to controller 28 to control the timing and the duration of the emission of x-ray beams 16 within the heart cycle from source 14. More particularly and in one embodiment, controller 28 includes a power supply (not shown) for supplying a high voltage anode-cathode signal to source 14. Utilizing the x-ray-on signal from circuit 100, the high voltage anode-cathode signal from the power supply may be quickly turned on and turned off so that x-ray beams 16 are respectively emitted and stopped from being emitted from source 14.

Figure 4:
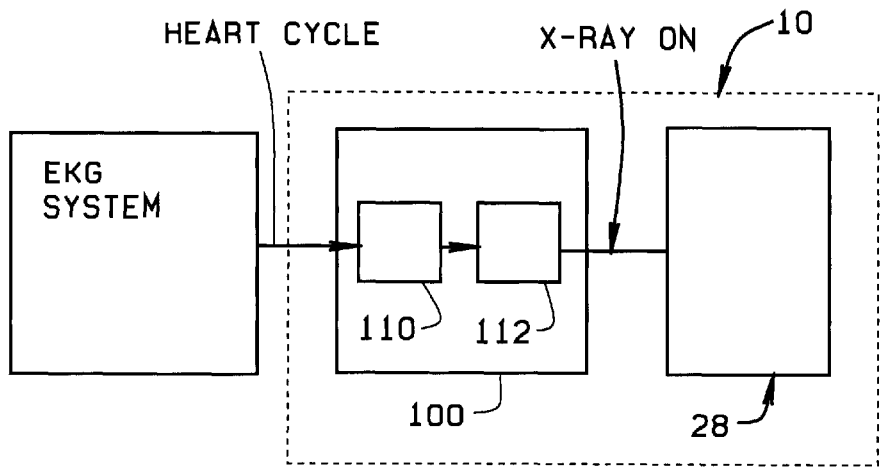
FIG. 4 is a synchronization circuit in accordance with one embodiment of the present invention.

Referring to FIG. 4 and in one embodiment, circuit 100, utilizing an adjustable level detector 110 and an adjustable timer, or delay 112, transitions the level of the x-ray-on signal during the selected period of the heart cycle by delaying a selected, or defined, period of time after the occurrence of an event in the heart cycle, i.e., the R-wave. For example, utilizing a known power supply having a high voltage output capable of being changed at a rate of approximately 75,000,000 volts per second, after detecting the R-wave, circuit 100 delays 0.5 second, then transitions the level of the x-ray-on signal supplied to controller 28 so that x-ray beams 16 are emitted from source 14 for 0.1 second. As a result, the high voltage anode-cathode output of the power supply transitions from approximately 0 volts to approximately 150,000 volts in approximately 0.002 second, remains approximately 150,000 volts for approximately 0.1 second, and returns to approximately 0 volts in approximately 0.002 second. During the time that the anode-cathode voltage is approximately 150,000 volts, x-ray beams 16 are emitted toward detector 18.

As x-ray beams 16 are emitted, projection data is collected for the selected period of the heart cycle. More specifically and in one embodiment, after determining the selected portion of the heart cycle, for example by an operator or a pre-defined period, projection data is collected using detector array 18 as x-ray beams 16 are emitted from source 14. Particularly, during the rotation of gantry 12, circuit 100 supplies the x-ray-on signal to controller 28 so that x-ray beams 16 are emitted toward detector 18 for at least one view, or ray, angle of the selected heart period. In one embodiment, depending upon the timing of the x-ray-on signal, the view, or ray, angle between source 14 and detector array 18 is altered so that projection data is collected from a series, or plurality, of view angles so that a complete image of the heart for the selected period is generated. More specifically, as a result of the normal variation in the heart rate from beat to beat, a series of view sector data, whose angle vary, is collected and stored, for example in computer 36, until sufficient data has been collected to generate a complete cross sectional view of the heart during the selected portion of the heart. After collecting the data, an image of the heart is generated using known methods, i.e., known weighting- filtering-backprojection methods.

For example, in one embodiment, x-ray beams 16 are emitted and data is collected when a minimum motion condition of the heart exists, i.e., the diastolic period. As result of the normal beat variation of the heart and the rotation of gantry 12, x-ray beams 16 are emitted at different angles with respect to patient 22. Therefore, data is collected from a plurality of angles so that a complete image of the heart at a minimum motion condition is generated.

In an alternative embodiment, images of other portions of the circulation system are generated during a selected portion of the heart cycle. Using the heart cycle, an image of a circulation system object is generated for the selected heart period. For example, using the heart cycle, an image may be generated of an artery during the selected period of the heart.

The above described imaging system gathers data during a selected period of the heart cycle so that image quality is improved. In addition, the imaging system controls the emission of x-ray beams so that x-ray dosage to the patient is reduced.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required. Accordingly, the spirit and scope of the invention are to be limited only by the terms of the appended claims.

What is claimed is:

1. A method for generating an image of an object in a computed tomography (CT) system, the CT system including an x-ray tube for emitting x-ray beams and a detector array, the detector array including a plurality of detectors aligned with the x-ray tube for receiving the x-ray beams, said method comprising the steps of:

determining a cycle of a heart;

generating at least one image view data of the object for at least one selected portion of the heart cycle; and generating at least one image of the object based on the image view data;

wherein the object is a portion of the circulation system other than the heart, and wherein generating image view data of the object for at least one selected portion of the heart cycle comprises the step of gating an x-ray on signal so that an anode-cathode voltage of the x-ray tube is cycled on for the selected portion of the heart cycle and cycled off after a defined period of time.

2. A method in accordance with claim 1 wherein the detector array is a multislice detector array, and generating image view data of the object for at least one selected portion of the heart cycle comprises the step of emitting an x-ray beam from the x-ray tube continuously towards the multislice detector array during times when the anode-cathode voltage of the x-ray tube is cycled on.

3. A method in accordance with claim 2 wherein the CT system comprises a rotating gantry on which the x-ray tube and detector array rotate, and further wherein:

generating image view data of the object for at least one selected portion of the heart cycle further comprises the step of utilizing beat variations of the heart and the rotation of the gantry to collect view data from a plurality of different angles with respect to a patient; and wherein generating at least one image of the object based on the image view data comprises generating a complete image of the heart at a minimum motion condition.

4. A method in accordance with claim 1 wherein determining a cycle of a heart comprises the step of determining at least a minimum motion condition of the heart.

5. A method in accordance with claim 4 wherein generating image view data of the object for at least one selected portion of the heart cycle comprises the step of generating image view data of the object for the minimum motion condition of the heart.

6. An imaging system for generating an image of an object, said imaging system comprising an x-ray tube for emitting x-ray beams and a detector array, said detector array including a plurality of detectors aligned with said x-ray tube for receiving said x-ray beams, said system configured to:

determine a cycle of a heart;

generate image view data of the object for at least one selected portion of the heart cycle; and generate at least one image of the object based on the image view data;

wherein the object is a portion of the circulation system other than the heart, and wherein to generate image view data of the object, said imaging system is configured to gate an x-ray on signal so that an anodic-cathode voltage of said x-ray tube is cycled on for the selected portion of the heart cycle and cycled off after a defined period of time.

7. An imaging system in accordance with claim 6 wherein said detector array is a multislice detector array, and to generate image view data of the object for at least one selected portion of the heart cycle said imaging system is further configured to emit an x-ray beam from said x-ray tube continuously towards said multislice detector array during times when the anode-cathode voltage of said x-ray tube is cycled on.

8. An imaging system in accordance with claim 7 wherein said imaging system further comprises a rotating gantry on which the x-ray tube and detector array rotate, and wherein:

to generate image view data of the object for at least one selected portion of the heart cycle, said imaging system is further configured to utilize beat variations of the heart and the rotation of the gantry to collect view data from a plurality of different angles with respect to a patient; and to generate at least one image of the object based on the image view data, said imaging system is further configured to generate a complete image of the heart at a minimum motion condition.

9. An imaging system in accordance with claim 6 wherein to determine a cycle of a heart, said system configured to determine at least a minimum motion condition of the heart.

10. An imaging system in accordance with claim 9 wherein to generate image view data of the object for at least one selected portion of the heart cycle, said system configured to generate image view data of the object for the minimum motion condition of the heart.

11. A method for generating an image of a portion of a circulation system other than a heart in a computed tomography (CT) system, the CT system including an x-ray tube for emitting x-ray beams and a detector array, the detector array including a plurality of detectors aligned with the x-ray tube for receiving the x-ray beams, said method comprising the steps of:

determining a cycle of a heart;

generating image view data of the portion of the circulation system other than the heart for at least one selected portion of the heart cycle; and generating at least one image of the portion of the circulation system other than the heart based on the image view data.

12. A method in accordance with claim 11 wherein generating image view data of the portion of the circulation system other than the heart comprises gating an x-ray beam emitted by the x-ray tube on and off in accordance with a selected portion of the cycle of the heart.

13. An imaging system for generating an image of a portion of a circulation system other than a heart, said imaging system comprising an x-ray tube for emitting x-ray beams and a detector array, said detector array including a plurality of detectors aligned with said x-ray tube for receiving said x-ray beams, said system configured to:

determine a cycle of a heart;

generate image view data of the portion of the circulation system other than the heart for at least one selected portion of the heart cycle; and generate at least one image of the portion of the circulation system other than the heart based on the image view data.

14. An imaging system in accordance with claim 13 wherein to generate the imaging view data, said imaging system is further configured to gate an x-ray beam emitted by said x-ray tube on and off in accordance with a selected portion of the cycle of the heart.

* * * * *

UNITED STATES PATENT AND TRADEMARK OFFICE
CERTIFICATE OF CORRECTION

PATENT NO. : 6,275,560 B1
DATED : August 14, 2001
INVENTOR(S) : Blake et al.

It is certified that error appears in the above-identified patent and that said Letters Patent is hereby corrected as shown below:

Column 5,
Line 30, delete "generating at least one image" and substitute -- generating image --.

Column 6,
Line 20, delete "anodic" and substitute -- anode --.

Signed and Sealed this

Fifth Day of November, 2002

Attest:

JAMES E. ROGAN
Attesting Officer
Director of the United States Patent and Trademark Office